United States Patent
Karpowicz et al.

(10) Patent No.: US 7,649,045 B2
(45) Date of Patent: Jan. 19, 2010

(54) MEDICAL FILMS AND ARTICLES PREPARED FROM EMULSION POLYMERS

(75) Inventors: Richard Karpowicz, Princeton, NJ (US); Alan I. Nakatani, Lansdale, PA (US); Katherine Sue Rice, Glenside, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 11/335,721

(22) Filed: Jan. 19, 2006

(65) Prior Publication Data

US 2006/0173111 A1 Aug. 3, 2006

Related U.S. Application Data

(60) Provisional application No. 60/648,234, filed on Jan. 28, 2005.

(51) Int. Cl.
*C09D 5/00* (2006.01)
*C08L 33/00* (2006.01)

(52) U.S. Cl. .................. 524/515; 524/500; 524/492

(58) Field of Classification Search ............... 524/539, 524/560, 563, 500, 515; 428/355 AC; 602/52
See application file for complete search history.

(56) References Cited

U.S. PATENT DOCUMENTS

| | | | |
|---|---|---|---|
| 4,246,387 A | 1/1981 | Deutsch | |
| 4,456,726 A | 6/1984 | Siol et al. | |
| 4,539,361 A | 9/1985 | Siol et al. | |
| 4,835,217 A * | 5/1989 | Jorgensen et al. | 525/93 |
| 5,120,325 A * | 6/1992 | Dow, Jr. | 604/304 |
| 5,308,890 A * | 5/1994 | Snyder | 523/201 |
| 5,340,858 A | 8/1994 | Bauer et al. | |
| 5,350,787 A | 9/1994 | Aydin et al. | |
| 5,352,720 A | 10/1994 | Aydin et al. | |
| 5,362,832 A | 11/1994 | Cook | |
| 5,656,286 A | 8/1997 | Miranda et al. | |
| 5,731,377 A * | 3/1998 | Friel | 524/522 |
| 5,958,446 A | 9/1999 | Miranda et al. | |
| 6,992,121 B1 * | 1/2006 | Peters et al. | 523/206 |
| 7,091,275 B1 | 8/2006 | Amick et al. | |
| 2003/0077443 A1 | 4/2003 | Di Stefano | |
| 2003/0143409 A1 * | 7/2003 | Di Stefano | 428/447 |
| 2003/0149119 A1 | 8/2003 | Schultz | |
| 2003/0175503 A1 | 9/2003 | Lucast et al. | |
| 2003/0180341 A1 | 9/2003 | Gooch et al. | |

FOREIGN PATENT DOCUMENTS

| | | |
|---|---|---|
| EP | 0 379 045 B1 | 7/1990 |
| EP | 1 473 311 A1 | 11/2004 |
| JP | 62-227435 A | 10/1987 |

* cited by examiner

*Primary Examiner*—David Wu
*Assistant Examiner*—Rip A. Lee
(74) *Attorney, Agent, or Firm*—Stephen T. Falk

(57) ABSTRACT

Protective film forming compositions useful as medical films and other related wound care and treatment articles, including liquid bandages are prepared from emulsion polymers, including a polymer blend including at least one hard emulsion polymer component and at least one soft emulsion polymer component, having the required dynamic storage modulus and mean Tg of the hard and soft polymer blend components.

13 Claims, No Drawings

MEDICAL FILMS AND ARTICLES PREPARED FROM EMULSION POLYMERS

CROSS REFERENCE TO RELATED PATENT APPLICATIONS

This is a non-provisional patent application of co-pending U.S. provisional patent application Ser. No. 60/648,234 filed Jan. 28, 2005.

This invention relates to film forming polymers useful as medical films and for preparing other medical articles. In particular, this invention relates to aqueous films prepared from blends of hard and soft emulsion polymers, which are useful for preparing medical film forming articles, including but not limited to films for covering and/or treating wounds to mammalian skin.

Liquid bandages are one type of medical articles used to protect a wound and assist its healing by applying a liquid over an injured area whereby the liquid dries and forms a tough but flexible film. The liquid bandages in use today or known by persons having skill in the relatively new art are designed from several different chemical systems that include: a) cyanoacrylate-based polymers that include one- and two-part systems having, unfortunately, limited utility; b) silicone and organic polymers that incorporate one or more solvents that result in a stinging sensation to the user; c) complex and hybrid polymers incorporating non-stinging silicone solvents or co-solvents, which as a consequence however, render the system essentially tack-free; and d) polymers prepared as mini-emulsions having, unfortunately, limited utility Conventional water-based pressure sensitive adhesives (PSAs) having exclusively soft domains prepared from acrylic based emulsion polymers typically do not provide films having the appropriate balance of tack, cohesive strength, film flexibilty and adhesion required for skin surfaces and related substrates. As well, acrylic based emulsion polymers having exclusively hard domains as a result of the monomer composition or mix polymers typically do not provide the appropriate balance of tack, shear and adhesion required for skin surfaces and related substrates.

U.S. Patent Application Publication No. 2003/0180341 A1 describes a polymer mini-emulsion for forming biocompatible hydrophilic films that are topically applied to mammalian skin or soft tissues comprising a dispersed phase of biocompatible polymer particles having an average particle size between 50 nm and 750 nm and that are prepared from ethylenically unsaturated monomers consisting of vinyl acetate and itaconic acid, an aqueous continuous phase in which the polymer is dispersed, and co-stabilizers effective to stabilize the mini-emulsion consisting of 2-ethylhexyl acrylate (EHA) and dioctyl maleate (DOM). Only one example of a mini-emulsion is disclosed that prepared at a low polymer solids level (<25 wt. %) and is required to have a solution viscosity less than 2000 centipoise. The mini-emulsion polymer, however, requires increased amounts of surfactants/emulsifiers (such as alkylaryl polyether alcohol and Nonlylphenoxy poly (ethyleneoxy) alcohol), wetting agents and other additives to stabilize the mini-emulsion. In addition, some of these additives are sensitizers for mammalian skin and certain other additives (hydropobes and plasticizers) may irritate or be toxic to open wounds. Moreover, the one example of a mini-emulsion polymer disclosed is likely not practical for commercial utility, since mini-emulsion polymers require specialized techniques and certain stabilizers for their preparation, that are not required for conventional emulsion polymers. Moreover, it is not likely the example of the mini-emulsion disclosed is tack-free, that is required for a medical film or an article such as liquid bandage. It is desirable, therefore, to provide medical films and articles, prepared from alternative aqueous emulsion polymers, that are easily applied directly to mammalian skin and related substrates. The polymers readily form a protective film over skin or a wound area, have the required reduction of tack, film flexibility and balance of adhesive properties as films to remain adhered to skin and related substrates until the wound has healed and provide an effective barrier to microorganisms, are resistant to water, are durable and washable, and permits air and moisture to contact the wound.

The inventors have discovered a simple yet unexpectedly effective adhesive composition that comprises a blend of at least two aqueous emulsion polymers, a hard polymer having an average particle size of greater than 30 nm, including but not limited to between 40 to 160 nm and a soft polymer having an average particle size less than 800 nm, including but not limited to between 360 to 480 nm. The adhesive composition forms a flexible, protective film directly upon mammalian skin and related substrates. The hard and soft ingredients are blended in the ratio of 5 parts hard to 95 parts soft, based on solids, to 60 parts hard and 40 parts soft, based on solids, and by varying the ratio of hard polymer components to soft polymer components, the tack is controlled and minimized over acrylic emulsion polymers, including mini-emulsions, that do not utilize such principles. The liquid emulsion polymer blend has utility as medical films and articles, including but not limited to, a protective film for covering skin and wounds, a skin and wound care device, a liquid bandage and combinations thereof.

The polymer blend is useful for preparing protective films and other medical articles due to a combinations of polymer properties including, but not limited to for example, film flexibility, namely, resistance to cracking during repeated and prolonged deformation (e.g. Bally™ flex testing) and effective rheology (e.g. dynamic storage modulus) that renders the resulting polymer films durable and flexible. Moreover, the polymer films exhibit tack equivalent to or better than existing commercial medical film forming products and sufficient moisture vapor transmission rates (MVTR) such that the substrates, including mammalian skin, mucosae and semi-mucosae, do not macerate when the films are used on human subjects. One advantage of the invention is that silicone solvents, silicone co-solvents, or silicone-based polymers are not required or used to reduce tack. It is believed that, without being bound by a particular theory or mechanism, the high Tg hard polymer particles effectively pack into the interstitial space of the large soft relatively lower Tg polymer particles upon film formation, rendering the surface less tacky versus either a single-polymer emulsion acrylic system or an acrylic blend not utilizing the differential particle size approach of the present invention, including many commercial liquid bandage products currently available and liquid bandage products incorporating complicated polymers to exhibit required mechanical properties of films prepared there from. Moreover the polymer blend of the invention provides films that maintain flexibility under prolonged deformation and that are water resistant.

Accordingly, the present invention provides one or more aqueous film forming compositions that adhere to mammalian skin and related substrates comprising: a blend of two or more polymers further comprising a) from 10 to 30% by weight of one or more hard polymers having a Tg greater than 37° C. and an average particle size greater than 30 nm; and b) from 70 to 90% by weight of one or more soft polymers having a Tg less than 37° C. and an average particle size less than 800 nm; wherein the polymer blend at 37° C. has a range of dynamic storage modulus (DSM) of from $5\times10^4$ and $1\times10^8$ dynes/cm$^2$ at a frequency of $10^{-1}$ rad/sec to a corresponding dynamic storage modulus of from $1\times10^6$ and $1\times10^8$ dynes/cm$^2$ at a frequency of $10^2$ rad/sec.

The invention also provides a method of forming a film that adheres to mammalian skin and related substrates comprising the steps of: (a) applying an aqueous dispersion of a blend of two or more emulsion polymers onto mammalian skin and related substrates, the polymer blend further comprising: i) from 10 to 30% by weight of one or more hard polymers having a Tg greater than 37° C., including but not limited to a Tg between 40 to 75° C., and an average particle size greater than 30 nm and ii) from 70 to 90% by weight of one or more soft polymers having a Tg less than 37° C., including but not limited to a Tg between 0 to 15° C., and an average particle size less than 800 nm; wherein the polymer blend at 37° C. has a range of dynamic storage modulus of from $5\times10^4$ and $1\times10^8$ dynes/cm$^2$ at a frequency of $10^{-1}$ rad/sec to a corresponding dynamic storage modulus of from $1\times10^6$ and $1\times10^8$ dynes/cm$^2$ at a frequency of $10^2$ rad/sec; and (b) drying the aqueous dispersion to form a continuous film that adheres to the area of mammalian skin and related substrates.

The invention also provides a liquid emulsion bandage that adheres to mammalian skin and related substrates comprising: a) from 10 to 30% by weight of one or more hard polymer particles having a Tg greater than 37° C., including but not limited to a Tg between 40 to 75° C., and an average particle size greater than 30 nm; and b) from 70 to 90% by weight of one or more soft polymers having a Tg less than 37° C., including but not limited to a Tg between 0 to 15° C., and an average particle size less than 800 nm; wherein the polymer blend at 37° C. has a range of dynamic storage modulus of from $5\times10^4$ and $1\times10^8$ dynes/cm$^2$ at a frequency of $10^{-1}$ rad/sec to a corresponding dynamic storage modulus of from $1\times10^6$ and $1\times10^8$ dynes/cm$^2$ at a frequency of $10^2$ rad/sec; and wherein the bandage is permeable to air and water, durable and washable.

The invention also provides film-forming compositions, and the corresponding films and articles prepared there from that further comprises one or more active agents.

The invention also provides an aqueous film forming adhesive composition further comprising one or more ethylenically unsaturated surfactant monomers.

As used herein, the term "film-forming" refers to a composition when allowed to dry under ambient conditions (e.g., 20 to 25° C. and 20-80% relative humidity) on intact skin forms a continuous layer that does not flake off after simple flexing of the tissue. As used herein, the term "related substrates" refers to any substrates, including but not limited to, any sensitive tissues related to mammalian skin in chemical composition, including but not limited to sensitive tissues such as mucosae, semi-mucusae and any substrates including polymers used to approximate mammalian skin. The term "wound" refers to an injury to mammalian tissue that involves breaking of a membrane such as the skin or mucosal surface usually with damage to underlying tissue arising from, but not limited to, a surgical incision, puncture, laceration, or burn. As used herein, the term "ethylenically unsaturated surfactant monomers" refers to monomers that when added to water reduces the surface tension of water to less than 72 dynes/cm. The ethylenically unsaturated groups of ethylenically unsaturated monomers used in the present invention are polymerized under conditions of emulsion polymerization described herein and are incorporated in aqueous emulsion polymers formed, including polymer blends and then subsequently used to prepare films and related articles of the invention. The aqueous film forming compositions prepared using the one or more ethylenically unsaturated surfactant monomers and films prepared there from provide alternative protective films and related medical articles that adhere to mammalian skin and related substrates.

The aqueous adhesive compositions of the present invention comprise a blend of one or more hard and soft aqueous emulsion polymers. The one or more hard polymer particles having a Tg greater than 37° C., including but not limited to a Tg between 40 to 75° C., and an average particle size greater than 30 nm, including but not limited to particle size from 40 nm to 160 nm. The one or more soft polymers having a Tg less than 37° C., including but not limited to a Tg between 0 to 15° C., and an average particle size less than 800 nm, including but not limited to between 360 to 480 nm. The one or more hard and soft polymers are prepared, as polymerized units, from at least one multiethylenically or ethylenically unsaturated monomer and at least one ethylenically unsaturated water soluble monomer. Optionally, the polymers further comprise at least one ethylenically unsaturated surfactant monomer As used herein, the term "dispersion" refers to a physical state of matter that includes at least two distinct phases wherein a first phase is distributed in a second phase, the second phase being a continuous medium. The term "aqueous" as used herein is meant the continuous medium that is from 50 to 100 wt. % water, based on the weight of the aqueous medium.

According to one embodiment of this invention, the aqueous adhesive composition includes a blend of two or more polymers further comprising: a) from 10 to 30% by weight of one or more hard polymers having a Tg between 40 to 75° C. and an average particle size greater than 30 nm; and b) from 70 to 90% by weight of one or more soft polymers having a Tg between 0 to 15° C. and an average particle size less than 800 nm; wherein the polymer blend at 37° C. has a range of dynamic storage modulus from $5\times10^4$ and $1\times10^8$ dynes/cm$^2$ at a frequency of $10^{-1}$ rad/sec to a corresponding dynamic storage modulus of from $1\times10^6$ and $1\times10^8$ dynes/cm$^2$ at a frequency of $10^2$ rad/sec. The components of the aqueous acrylic emulsion polymer blend comprise hard and soft emulsion polymers. Each respective component emulsion polymers comprise, as copolymerized units, one or more monoethylenically-unsaturated non-ionic (meth)acrylic monomers including esters, amides, and nitriles of (meth)acrylic acid, such as, for example, (meth)acrylic ester monomers including methyl acrylate, ethyl acrylate, butyl acrylate, 2-ethylhexyl acrylate (EHA), iso-octyl acrylate, decyl acrylate, lauryl acrylate, stearyl acrylate, hydroxy ethyl acrylate (HEA), methyl methacrylate, butyl methacrylate, hydroxyethyl methacrylate, hydroxypropyl methacrylate; urieido (meth)acrylate; (meth)acrylonitrile and(meth)acrylamide. The use of the term "(meth)" followed by another term such as acrylate, acrylonitrile, or acrylamide, as used throughout the disclosure, refers to both acrylate, acrylonitrile, or acrylamide and methacrylate, methacrylonitrile, and methacrylamide, respectively. By "non-ionic monomer" herein is meant that the copolymerized monomer residue does not bear an ionic charge between pH=1-14.

A wide variety of monomers or mixture of monomers may be used to make each respective hard and soft emulsion polymer used as a blend in the aqueous adhesives of this invention. Other suitable acrylic ester monomers, include but are not limited to for example, propyl acrylate, isopropyl acrylate, isobutyl acrylate, secondary butyl acrylate, t-butyl acrylate, pentyl acrylate, neopentyl acrylate, hexyl acrylate, heptyl acrylate, octyl acrylate, isodecyl acrylate, bornyl acrylate, isobornyl acrylate, myristyl acrylate, pentadecyl acrylate and the like; likewise other methacrylic acid ester monomers, including but not limited to, ethyl methacrylate, propyl methacrylate, isopropyl methacrylate, isobutyl methacrylate, hexyl methacrylate, octyl methacrylate, isooctyl methacrylate, decyl methacrylate, isodecyl methacrylate, lauryl methacrylate, bornyl methacrylate, isobornyl methacrylate, myristyl methacrylate, pentadecyl methacrylate, stearyl methacrylate, phosphoethyl methacrylate and the like; maleate esters and the like may be used.

According to an alternate embodiment of the invention, amine group-containing monomers (i.e., amine-containing), including monomers incorporating side-chains and hydrophobic character are usefully employed as hard, soft and combinations of hard and soft components of polymer blends useful in accordance with the present invention. The amine groups can be quaternary amine (i.e., quaternary ammonium) groups, amine oxide groups, and/or protonated tertiary amine groups.

Exemplary hard/soft emulsion polymer components useful for preparing required polymer blends of the invention and methods used for preparing the polymers is described in U.S. Pat. No. 5,731,377. According to one embodiment of the present invention, the hard/soft polymer components of the polymer blend have the required rheology for preparing protective films and related articles of the invention that in turn have corresponding required mechanical properties, adhesion, flexibility and dynamic storage modulus. According to another embodiment, the emulsion polymer comprises a blended system of hard/soft emulsion polymers having similar particle size (~90 nm). According to a separate embodiment, the polymer blend is modified with the soft component polymer by adding more hard monomer, while still maintaining favorable film characteristics of flexibility (as developed and measured by dynamic mechanical analysis (DMA). The utility of the particle size differential as applied to tack reduction was discovered to provide optimized medical films and related articles, since it was observed that conventional emulsion polymers or blends of acrylic emulsion polymers not utilizing the differential particle size approach of the invention while film forming, however, still attracted particulates (e.g. dirt, bacteria) due to their inherent low-level of tack.

According to one embodiment of the invention, an aqueous medical film forming composition is prepared from acrylic emulsion polymer technology in the form of a blend of at least two polymers, the first being a hard polymer with a Tg of +63° C., as measured by differential scanning calorimetry DSC, and a composition of 27 BA/70.5 Sty/2 MAA/0.5 urieido (meth)acrylate, with an average particle size between 40 nm to 160 nm, and the second polymer component being a soft component, with a Tg of 9° C. by DSC, a composition of 60 BA/36.5 Sty/2.5 MAA/1 urieido (meth)acrylate, and an average particle size between 360 to 480 nm. The hard and soft ingredients are blended in the ratio of 10 parts hard to 90 parts soft, based on solids, to 30 parts hard and 70 parts soft, based on solids, and by varying the ratio, the tack is controlled and minimized over acrylic emulsion polymers that do not utilize this principal. Silicone solvents, silicone co-solvents, or silicone-based polymers are not required or not used to reduce tack. Rather, while not being bound to particular theory or mechanism, it is believed that the high Tg hard particles effectively pack into the interstitial space of the large soft particles upon film formation, rendering the surface less tacky as compared to either a single-polymer emulsion acrylic system or an acrylic blend not utilizing the differential particle size approach, or many commercial products currently on the market (for example, less tacky than Curad™, and equivalent to adhesives that incorporates a very complicated and sophisticated approach to tack reduction). Once dry, the resulting films of the invention exhibit favorable mechanical properties that permit the films to stay flexible and water resistant.

One advantage is the present invention utilizes a blend of water-based emulsion polymers that comprise a single polymer system, as compared to medical adhesives comprising two-part polymer systems (e.g. cyanoacrylate polymers described in the prior art). The present invention also utilizes safer, non-stinging, water as the medium for the film forming polymers. The present invention provides film forming polymers to prepare films having good integrity, flexibility, and reduced to no tack using a hard/soft particle size differential. Another advantage of the polymer blends of the present invention is that monomers such as EHA are used to modify rheology of the blend as compared to polymers requiring them as a required co-monomer necessary to stabilize the polymers of the prior art.

The current invention describes a new approach to preparing medical films that is different in two ways from the prior art. First, the invention controls tack by blending a small hard acrylic polymer with a large soft polymer. Secondly, the current invention is an oil-in-water emulsion that does not utilize a silicone polymer to cover a tacky component and render the surface non-tacky.

Films prepared from the liquid emulsion polymers, including polymer blends, have utility as protective films and related wound care articles due to a combinations of factors including, but not limited to for example, that the polymer blends are designed to provide films exhibiting polymer properties including, but not limited to for example, film flexibility, namely, resistance to cracking during repeated and prolonged deformation (e.g. Bally™ flex testing) and effective rheology (e.g. dynamic storage modulus) that renders the resulting polymer films durable and flexible. Moreover, the films exhibit tack equivalent to or better than existing commercial medical products and sufficient moisture vapor transmission rate (MVTR) such that the substrates, including mammalian skin do not macerate when the films are used on human subjects.

Medically useful film-forming compositions of the present invention and the films and articles prepared there from are suitable for topical administration to skin and related substrates, including sensitive tissues such as mucosae and semi-mucosae.

According to one embodiment, medically useful compositions are prepared as antiseptic compositions and have the following characteristics: relatively high levels of bacterial kill if an antimicrobial agent is present or if the composition is inherently antimicrobial; relatively short dry times; generally clear viewing of the underlying tissue; good adhesion to the skin when dry; little to no tack when dry; capable of releasing one or more active agents such as an antimicrobial agent over a period of time; resist lift off coated products while under stress as typically occurs during retraction in surgery; allow adhesion of coated products for long periods of time, e.g., hours to days; suitable for use on sensitive tissues such as mucosal tissue; and can be removed relatively easily, preferably without the need for organic solvent-based removers. Alternatively, they can be manufactured as pressure sensitive adhesives (PSAs) such as tapes, wound dressings, and the like.

Film-forming compositions, and the corresponding films and articles prepared there from that include at least one active ingredient possess all of the above-mentioned characteristics. They also provide rapid microbial kill (if the composition of the present invention is an antiseptic composition), and they dry to low tack or non-tacky films, which provide good adhesion. Alternatively, the polymer blends can be prepared as PSAs. Furthermore, they are gentle to tissue and can be removed with a water-soaked fabric, such as a towel or simple gauze.

Film-forming compositions, and the corresponding films and articles prepared there from of the present invention are stable and can survive prolonged exposure to elevated temperatures, e.g., >37° C., for prolonged periods of time, e.g., greater than 7 days. The most stable films show no visible changes at all such as changes in color, turbidity, or cracking of the film. Also, film-forming compositions, and the corresponding films and articles prepared there from of the present invention are stable upon exposure to low temperatures, e.g., <37° C., and even during repeated freeze/thaw cycles.

According to one embodiment, the composition includes an active agent. Active agents include but are not limited to one or more antimicrobial agents, pharmaceutical agents, cosmetic agents, skin care agents and combinations thereof. A suitable example of an antimicrobial agent is iodine or an iodophor such as povidone-iodine, chlorhexidine, chlorhexidine salts, fatty acid monoesters of glycerin and propylene glycol, chlorinated phenols, triclosan, octenidine, or mixtures thereof.

Film-forming compositions, and the corresponding films and articles prepared there from of the present invention are also generally substantive. Certain film-forming compositions, and the corresponding films and articles prepared there from are substantive while in moist environments, including sensitive tissues and remain there for longer periods of time than typical antiseptics such as BETADINE™ 10% povidone-iodine solution (Purdue Frederick, Norwalk, Conn.). A substantive film-forming compositions, and the corresponding films and articles prepared there from is conveniently determined by imparting color to the composition (e.g., inclusion of a small amount of a dye or a colored active such as povidone-iodine in sufficient concentration that a relatively dark color results on the skin that can be easily seen as present or not).

Dried and/or coated films and articles prepared from film-forming compositions, and the corresponding films and articles prepared there from of the present invention are generally flexible and durable. That is, they do not crack or flake off as prior art films might do. Significantly, the film-forming polymer blend contributes to achieving a delicate balance between low tack and flexibility.

Any suitable pharmaceutical agent, including combinations of pharmaceutical agents may be usefully included in film-forming compositions, and the corresponding films and articles prepared there from of the present invention. Suitable examples include topical antibacterial agents.

Any suitable cosmetic agent, including combinations of cosmetic agents may be usefully included in film-forming compositions, and the corresponding films and articles prepared there from of the present invention. Suitable examples include fragrances, perfumes, vitamins, UV active substances, whiteners, retinols, alpha-hydroxy acids, anti-wrinkle agents, enzymes, colorants, dyes, emollients, humectants, oils, flavors, natural extracts, silicones lipids, and any other suitable cosmetic agent.

Any suitable skin care agent, including combinations of skin care agents may be usefully included in film-forming compositions, and the corresponding films and articles prepared there from of the present invention. Suitable examples include cleaners, washes, foams, deodorants, oxidants, sunscreens, and moisurizers.

The invention includes the following advantageous mechanical properties over the prior art:

Mechanical properties of the films prepared from polymer blends of the invention that exhibit improved flexibility can be explained via rheological "windows" of the storage modulus and Tan Delta (tan δ) functions versus frequency. A large body of data is provided in the Examples concerning this feature.

Mechanical properties that render films of the present invention suitably durable are evidenced and gathered from wear test experiments and end user feedback and required testing including clinical trials and toxicological testing and other mechanical property evaluation such as abrasion testing.

The emulsion polymer blends incorporating differential particle sizes, versus a single polymer approach or blends using similar particle sizes, is advantageous when reducing tack in films prepared from such polymers. Two ways to make a polymer less tacky, for example, are to increase the amounts or proportion of hard monomers to soft monomers in the polymer blend, or to blend in hard polymers having small particle sizes), the latter has advantages due to maintaining favorable flexibility versus the former approach. Ancillary evidence is provided from rheological data. MVTR correlates with the fact that the skin does not macerate when the adhesive articles of the invention are worn by users. According to an exemplary embodiment, measured MVTR and obtained values of around 600 $g/m^2/24$ h for films between 0.5 and 1 mil thick.

It is contemplated that functional group contributions to skin adhesion and water resistance can be assessed using leather Satra tests.

According to a separate embodiment of the invention, the hard and soft aqueous emulsion polymer components also includes, as copolymerized units, from 0.25% to 30% by weight, based on polymer weight, of one or more ethylenically unsaturated surfactant monomers. The ethylenically unsaturated surfactant monomers are surface active agents and are especially useful in emulsion polymerization reactions and are generally capable of co-polymerizing with other ethylenically unsaturated monomers which are conventionally employed in emulsion polymerization reactions, and are capable of polymerizing with themselves, or co-polymerization with a partially polymerized polymer.

Suitable ethylenically unsaturated surfactant monomers include, but are not limited to, for example, salts or quaternary nitrogen compounds comprising at least one acid, wherein the acid is a sulfonic acid, a carboxylic acid, or a phosphoric acid, or a mixture thereof, and at least one nitrogenous base, wherein the nitrogenous base contains at least one nitrogen atom and at least on ethylenically unsaturated moiety. Other suitable examples are described in U.S. Pat. Publ. No. 2003/0149119.

Other suitable polymerizable surfactant monomers include nonylphenoxy propenyl polyethoxylated sulphate (for example as Hitenol™ from Daiichi Corp); sodium alkyl allyl sulphosuccinate (for example as Trem™ LF-40 from Henkel Corp); ammonium di-(tricyclo(5.2.1.0 2,6) dec-3-en-(8 or 9)oxyethyl) sulfosuccinate; and ammonium di-(tricyclo (5.2.1.0 2,6) dec-3-en-(8 or 9) sulfosuccinate. Additionally, the ammonium and metal salts of unsaturated $C_6$ to $C_{30}$ organic acids can be used, alone or in combination with the above surfactants. Examples of these acids are: alpha methyl cinnamic acid, alpha phenyl cinnamic acid, oleic acid, linoleic acid (as described in U.S. Pat. No. 5,362,832), rincinoleic acid, the unsaturated fraction of Tall oil rosin and fatty acids, disproportionated rosin acid, soybean oil fatty acids, olive oil fatty acids, sunflower oil fatty acids, linseed oil fatty acids, safflower oil fatty acids, sorbitan mono-oleate, abietic acid, poly(oxyethylene) sorbitol sesquioleate, and Empol 1010 Dimer Acid. Additional suitable polymerizable surfactant monomers also include, for example, maleate derivatives (as described in U.S. Pat. No. 4,246,387), and allyl derivatives of alkyl phenol ethoxylates (as described in Japa. Pat. No. 62-227435). The amount of surfactant used is typically from 0.1% to 20% including from 0.25% to 6% by weight, based on the total weight of monomer.

The hard and soft aqueous emulsion polymer components of the blend also contains, as copolymerized units, from 0.25% to 10% by weight, based on dry polymer weight, monoethylenically-unsaturated acid monomer such as, for example, acrylic acid, methacrylic acid, crotonic acid, itaconic acid, sulfoethyl methacrylate, phosphoethyl methacrylate (PEM), fumaric acid, maleic acid, monomethyl itaconate, monomethyl fumarate, monobutyl fumarate, and maleic anhydride. Preferably, the emulsion polymer contains, as copolymerized units, from 0.3% to 2.5% by weight, based on dry polymer weight, (meth) acrylic acid.

The hard and soft aqueous emulsion polymer components of the polymer blend further contains, as copolymerized units, from 0 to 49.75% by weight, based on dry polymer weight, of optional monomers which are neither non-ionic monoethylenically unsaturated (meth)acrylic monomers nor monoethylenically unsaturated acid monomers. Optional monomers include, for example, styrene or alkyl-substituted styrenes; butadiene; aminoalkyl (meth)acrylate, N-alkyl aminoalkyl (meth)acrylate, N,N-dialkyl aminoalkyl (meth)acrylate; vinyl acetate, vinyl propionate, or other vinyl esters; vinyl monomers such as vinyl chloride, vinylidene chloride, and N-vinyl pyrollidone; allyl methacrylate, vinyl toluene, vinyl benzophenone, diallyl phthalate, 1,3-butylene glycol dimethacrylate, 1,6-hexanedioldiacrylate, and divinyl benzene.

The emulsion polymer used in this invention is substantially uncross-linked, when it is applied to a substrate in the method of this invention, although low levels of deliberate or adventitious cross-linking can be present. When low levels of cross-linking or gel content are desired low levels of optional non-ionic multiethylenically unsaturated monomers such as, for example, 0% to 5% by weight, including 0.05 to 1% by weight, based on the dry polymer weight, can be used. The terminology "multiethylenically unsaturated" means having two or more sites of ethylenic unsaturation per molecule. Suitable multiethylenically unsaturated monomers include, for example, allyl (meth)acrylate, diallyl phthalate, 1,4-butylene glycol di(meth)acrylate, trimethylolpropane tri(meth)acrylate, divinyl ketone, N,N'-methylenediacrylimide, the polyallyl and polyvinyl ethers of pentaerythritol and mixtures thereof.

The acrylic emulsion polymers including emulsion polymer blends can be made by various solution, suspension, inversion and emulsion polymerization techniques known in the art and combinations thereof for polymerizing ethylenically unsaturated monomers. According to one embodiment, the emulsion polymer is made by a free-radical initiated aqueous emulsion polymerization. Such techniques are well known in the art and are described in is described in U.S. Pat. No. 5,731,377 and references cited therein.

Typically, the initiator and the monomers to be polymerized in the emulsion polymerization are added to an aqueous medium at controlled rates and the polymerization is carried out in the presence of a stabilizer. However, the use of polymerizable surfactant monomers render the addition of stabilizers unnecessary.

In the preparation of the aqueous hard and soft acrylic emulsion polymer components of the polymer blend, a thermal initiation process is used. The thermal initiator provides free radicals at a useful rate at the reaction temperature. The reaction temperature is maintained at a temperature from 70° C. to 99° C. throughout the course of the reaction. Preferred is a reaction temperature between 75° C. and 95° C., more preferably between 80° C. and 90° C. The reaction temperature can be held at a constant temperature or varied throughout part or all of the reaction as desired. The reaction is typically carried out at a pH of from 2 to 8. The monomer mixture can be added neat or as an emulsion in water. The monomer mixture can be added in one or more additions or continuously, linearly or not, over the reaction period, or combinations thereof. Useful initiators include, for example, sodium persulfate, potassium persulfate, ammonium persulfate, sodium perborate, and ammonium or alkali metal peroxydisulfate salts. Preferred are persulfate salts. The thermal initiation can be augmented by a minor amount of a redox initiated reaction which is effected when the thermal initiator, also known in the art as an oxidant, is contacted with a reductant. Suitable reductants include, for example, sodium sulfoxylate formaldehyde, alkali metal and ammonium salts of sulfur-containing acids, such as sodium sulfite, bisulfite, thiosulfate, hydrosulfite, sulfide, hydrosulfide or dithionite, formadinesulfinic acid, hydroxymethanesulfonic acid, acetone bisulfite, amines such as ethanolamine, glycolic acid, glyoxylic acid hydrate, ascorbic acid, isoascorbic acid, lactic acid, glyceric acid, malic acid, 2-hydroxy-2-sulfinatoacetic acid, tartaric acid and salts of the preceding acids. Redox reaction catalyzing metal salts of iron, copper, manganese, silver, platinum, vanadium, nickel, chromium, palladium, or cobalt can optionally be used. In any event the reaction includes less than 0.5 moles, preferably less than 0.2 moles, more preferably less than 0.1 mole, and most preferably no moles of reductant per mole of thermal initiator. The thermal initiator is used in the amount of from 0.3% to 4.0%, by weight, based on dry polymer weight. According to one embodiment, the thermal initiator is used in the amount of from 0.05% to 0.3%, by weight, based on dry polymer weight.

Other suitable free radical initiators include known peroxides, hydroperoxides, persulfates and azo initiators such as, for example, hydrogen peroxide, benzoyl peroxide, tert-butyl hydroperoxide, tert-amyl hydroperoxide, cumene peroxide, tert-butyl perbenzoate, tert-butyl diperphthalate and methyl ethyl ketone peroxide, ammonium persulfate, sodium persulfate, potassium persulfate, azodiisobutyronitrile and mixtures thereof. The initiators can be used alone, i.e., in a thermal initiation system, or, optionally, in combination with a reducing agent, i.e., in a redox initiation system. The initiator is preferably used at a level of from about 0.01 parts per weight (pbw) to 3 pbw per 100 pbw total monomer charge. As used herein, the terminology "total monomer charge" means all monomers added to the aqueous medium during the course of the polymerization process.

A chain transfer agent may be usefully employed in accordance with the invention. The weight average molecular weight (Mw) of the emulsion polymer may be adjusted through the addition of a chain transfer agent, such as n-dodecyl mercaptan, during emulsion polymerization to give a suitable balance of adhesive and cohesive strength. Suitable chain transfer agents include, but are not limited to for example, isopropanol, halogenated compounds, n-butyl mercaptan, n-amyl mercaptan, n-dodecyl mercaptan, t-dodecyl mercaptan, alkyl thioglycolate, mercaptopropionic acid, and alkyl mercaptoalkanoate. According to one embodiment of the invention, chain transfer agent is not required but in some embodiments it is used in an amount of from 0.001 to 0.05, including from 0.0025 to 0.05, moles per kg dry polymer weight. Linear or branched $C_4$-$C_{22}$ alkyl mercaptans such as n-dodecyl mercaptan and t-dodecyl mercaptan are preferred. Chain transfer agent(s) can be added in one or more additions or continuously, linearly or not, over most or all of the entire reaction period or during limited portion(s) of the reaction period such as, for example, in the kettle charge and in the reduction of residual monomer stage.

In the preparation of the aqueous acrylic emulsion polymer a neutralizer may be included. By "neutralizer" herein is meant a basic material which is capable of entering into an acid-base reaction with the acid monomer. Suitable neutralizers include, for example, ammonia, amines, sodium hydroxide, potassium carbonate, and sodium bicarbonate. The neutralizer is used in the amount of from 5% to 75%, preferably from 5% to 50%, on an equivalents basis, based on the equivalents of monoethylenically unsaturated acid monomer.

Particle sizes herein are those determined using a Brookhaven Model BI-90 particle sizer manufactured by Brookhaven Instruments Corporation, Holtsville N.Y., reported as "effective diameter". Also contemplated are multimodal particle size emulsion polymers wherein two or more distinct particle sizes or very broad distributions are provided as is taught in U.S. Pat. Nos. 5,340,858; 5,350,787; 5,352,720; 4,539,361; and 4,456,726.

The adhesive, film forming composition may in some embodiments may contain conventional adhesive adjuvants such as, for example, tackifiers, emulsifiers and wetting agents, cross-linkers, monomers, oligomers, polymers, solvents or plasticizers, buffers, neutralizers, thickeners or rheology modifiers, biocides, antifoaming or defoaming agents. They may, optionally, further include other additives known in the art such as, for example, pigments, fillers, curing agents, adhesion promoters, colorants, waxes and antioxidants and other conventional additives.

The solids content of the aqueous film forming compositions of the present invention can be from about 10% to about 80% by weight. The viscosity is typically from 0.05 to 5 Pa.s (50 cps to 5000 cps), as measured using a Brookfield viscometer; the viscosities appropriate for different end uses and application methods vary considerably. The film are applied directly to mammalian skin and related substances from any aqueous dispersions of the polymers, including gels and foams. The polymers are applied by conventional methods including but not limited to finger application, by brush, pump spray, aerosol sprays.

Aqueous adhesive compositions with desirable gas or moisture barrier properties can be prepared using polymerizable, ethylenically unsaturated surface active monomers and suitable monomers including but not limited to for example vinyl chloride, vinylidene chloride, vinyl alcohol, acrylonitrile and other monomers known to provide barrier functionality when incorporated in suitable polymers.

Compounds that absorb or retain moisture and that are non-volatile and compatible with the acrylic polymer under the conditions of anticipated use are useful as the humectant of the adhesive composition of the present invention. Suitable humectants include but are not limited to, for example, protein based humectants such as urea and urea derivatives, polyols, including poly(oxyalkylene) glycols, ethoxylated polyols and propoxylated polyols, sugars, including ethoxylated sugars and propoxylated sugars, 1,3-butane diol, 1,2,6-hexanetriol, trimethylol propane, pentaerythritol, glycerol, polyethylene glycols having a molecular weight of from about 100 to about 4000 g/mol, such as, for example, diethylene glycol and triethylene glycol, poly(ethylene oxide/propylene oxide) copolymers, sorbitol, glucose, sucrose, corn syrup, ethoxylated (10-40 moles ethylene oxide) glycerol, ethoxylated (10-40 moles ethylene oxide) glucose, propoxylated (10-40 moles propylene oxide) glucose, hydrolyzed soy protein, soluble collagen and mixtures thereof.

The following examples are presented to illustrate further various aspects of the present invention.

EXAMPLE 1A

Blend of 20 hard /H80 soft polymer particles ~94 nm both hard and soft by BI-90 technique. (All ratios are solids on solids by weight.)

Composition hard polymer=27 BA/70.5 Sty/2 MAA/0.5 ureido methacrylate [hard, ~94 nm PS]

Composition soft polymer=60 BA/36.5 Sty/2.5 MAA/1 ureido methacrylate [soft, ~94 nm PS]

Notes: under the conditions shown, this hard/soft blend averaged about 450 g of release force after debonding from the surface. This is what is referred to as "tack." Probe makes contact with sample and enters sample until 500 grams of force is reached, then the contact time is 2 seconds, when probe releases at a defined rate of 0.2 mm/sec, which results in a maximum force upon debonding probe with surface of the film sample.

EXAMPLE 1B

Blend of 20 hard (at 42 nm)//80 soft (at 363 nm). PS measured by BI-90 technique.

Composition hard polymer=27 BA/70.5 Sty/2 MAA/0.5 ureido methacrylate [hard, ~42 nm PS]

Composition soft polymer=60 BA/36.5 Sty/2.5 MAA/1 ureido methacrylate [soft, ~363 nm PS]

The overall compositions of these polymers are the same as their respective hard/soft 94 nm polymer analogues.

The hard/soft blend averaged about 69 g of release force or "tack."

The differences appear to be real in that the Standard Deviations preclude data overlap. These differences are therefore real.

EXAMPLE 2

Comparison of (20 Hard at 42 nm //80 Soft at 363 nm) and (20 Hard at 94 nm//80 soft at 94 nm). Compositions otherwise identical as previously stated.

On the same scale, one can see demonstrated the difference in the tack reduction using the small hard//large soft approach.

Experimental: 5.0 grams of liquid water-based emulsion 40 and 45% solids were cast in 5.3 cm ID plastic petri dishes (usually) and set on a level table then allowed to dry. Initial weights were recorded to confirm the percent of drying. Samples were usually air dried for periods up to a week. In other cases, samples were air dried and then gently oven warmed for several hours to overnight, and in still other cases samples were air dried for several days then placed in a vacuum oven overnight. Theoretical thicknesses are in the order of ~1 mm thick.

Surface Tack Testing

Reduction in tack quantitatively by employing a Texture Technologies Corporation TA XT Plus instrument employing a 7 mm stainless steel probe. A diagram shows the concept (not to scale). The force when the probe exits the surface of the sample is measured, according to prescribed conditions, giving a direct measure of surface tack of a film.

Experiments with drying technique and often found differences in the absolute magnitude of the peaks from one sample preparation to the next, but the reduction in tack was always observed when similarly prepared sample types of the equal particle size and non-equal particle size were compared, as demonstrated above.

Details:

The film was cast and dried as above, and data was acquired within a Petri dish sample by at least five, but usually ten, separate probe runs in different locations on the sample surface. The system was warmed up and calibrated prior to data acquisition. The probe was cleaned with isopropyl alcohol between each run, and prior to any single probe run, the probe height was recalibrated each time prior to the individual data acquisition, and the data was acquired in the same spot the calibration took place.

Title: Preparation and tack analysis of ternary blends for liquid bandage patent.
Purpose: To prepare bulk samples of ternary blends and determine tack using 12, 25, and 50 nm Klebosols.
Reference: Q:\MEDAD_2\Liquid Bandage\TA Testing\9_24_04Ternaryblends_TA.xls
"A" sample run unless otherwise noted, final prep weights are listed for duplicates A and B.
Conclusions: All samples were compared to the contols in terms of tack. The HO69-01 is the standard 90 nm hard/90 nm soft blend, and HO1-01 was added as an additional control since it is an analogue of the HO69-01 with different particle sizes. The data suggests that the 12 nm Klebosol shows the best degree of reduction in tack as compared to the blends made with the larger particle sized Klebosols. In each case, the binary blend of 0_6854/70_6858/30_Klebosol X shows a reduction in tack. The 10/70/20 ternary hard/soft ratio shows a tack reduction in the 12 and 25 nm systems. It did not seem to hold true for the 50 nm system.

| Sample ID | Force (grams) Avg | S.D. |
|---|---|---|
| HO1_01B | 3.071 | 1.972 |
| HO69_01 | 489.475 | 71.983 |
| HO84_01 | 282.317 | 72.355 |
| HO84_02 | 152.381 | 43.645 |
| HO84_03 | 19.12 | 13.427 |
| HO84_04 | 678.692 | 223.586 |
| HO84_05 | 49.508 | 31.464 |
| HO84_06 | 194.018 | 52.561 |
| HO84_07 | 583.921 | 140.061 |
| HO84_08 | 300.242 | 93.172 |
| HO84_09 | 51.674 | 20.468 |
| HO84_10 | 837.775 | 91.922 |
| HO84_11 | 222.754 | 72.013 |
| HO84_12 | 474.351 | 129.326 |
| HO84_13 | 742.443 | 140.845 |
| HO84_14 | 720.648 | 113.182 |
| HO84_15 | 700.576 | 200.613 |
| HO84_16B | 1918.633 | 331.525 |

-continued

| Sample ID | Force (grams) Avg | S.D. |
|---|---|---|
| HO84_17 | 856.147 | 102.911 |
| HO84_18 | 1179.713 | 144.584 |

Samples were prepared by drawing down the emulsions in plastic or teflon Petri dishes. The samples were allowed to air dry for 48 h, then placed on dry ice to remove the resultant films from the Petri dishes. The films were inverted in the dishes then allowed to air dry for an additional 48 h. Due to concerns about the potential for thermal crosslinking, the samples were not placed in a vaccum oven for additional drying. This was deemed suitable by the user.

All samples were tested on the Rheometrics Mechanical Spectrometer (RMS-800) using 8 mm parallel plate fixtures in the Dynamic Frequency Sweep Mode. An applied strain of 1% was used for all testing and an applied frequency of 6.28 rad/s. All samples were loaded at 67° C. to ensure good adhesion of the samples to the fixtures. The instrument was then cooled to the test temperature of 37° C. and allowed to equilibrate before initiating the test sequence. All samples were tested in duplicate, with a fresh sample used for each run. The average values for the dynamic storage and loss moduli as well as the complex modulus of the two runs for each sample are shown below. The error bars represent ±one standard deviation of the data set.

Alternatively, the Rheometrics Mechanical Spectrometer (RMS-800) was used in Dynamic Temperature Ramp mode to measure G', G" and tan δ as a function of temperature for all samples. Eight mm parallel plate geometry was used for all testing. The plates were gapped at 100° C. The sample was prepared by placing the Petri dish with the film on dry ice then using a 3/8" metal punch to punch a sample disc out from the film. The upper fixture was then lowered so the upper plate compressed the disc of sample. The sample is allowed to equilibrate at 100° C. until the normal force indicator remains constant. Once the sample has equilibrated, the gap is readjusted so zero normal force is registered on the sample. The test sequence is then initiated. The applied frequency for testing was 6.28 rad/s. A heating rate of 2° C./min was used, with a sampling frequency of one data point every 15 s. The AutoTension and AutoStrain options were both employed. The AutoTension direction was Compression with a Sensitivity setting of 8 g. The initial commanded strain for the experiment was 1% with minimum and maximum torque limits of 0.35 g-cm and 150 g-cm, respectively and a maximum strain of 5% for AutoStrain with an adjustment of 40% of the current value.

Dynamic storage modulus data for both Examples and comparatives clearly indicate utility of films of the present invention. A window of acceptable dynamic storage modulus values were defined at two frequencies, the $10^{-1}$ rad/sec low frequency G' window and the the $10^2$ rad/sec high frequency G' window to better accommodate the differential particle size blends to prove the point that the small hard polymer components can reduce tack. Also, addition of plasticizer and other additives will lower G', with $5\times10^4$ to $1\times10^8$ dyn/cm as the low frequency window. A polymer blend incorporating a lower Tg hard small polymer particle (<50 nm) will also lower G' storage modulus.

Data demonstrating the feasability of the rheological window as defined. Those materials in or close to the window parameters are most useful as film formers used on the skin because they crack slightly or not at all. Those materials with low tack are hard films exhibiting high G' storage modulus, and crack. Those materials with higher tack values are softer films with lower G' storage modulus values, exhibiting more flexibility.

| Sample | Hard/Soft Blend Ratio (on solids by weight) [particle sizes] | Fits in Rheological Window? | Tack[a] (g) | Bally Flex Test Observations[b] |
|---|---|---|---|---|
| A | 40:60 [42 nm:401 nm] | outside | 0.15 | Very hard and cracked on leather swatch prior to flex-testing |
| B | 30:70 [42 nm:401 nm] | outside | 0.41 | Severe cracking on swatch during flex test |
| C | 20:80 [42 nm:401 nm] | inside window | 2.93 | Slight to moderate cracking after test—needing microscope to see cracks |
| D | 15:85 [42 nm:401 nm] | inside window | 78.04 | Very slight to no cracking at center of swatch (the most flexed portion)—microscope needed for observation [c] |
| E | 5:95 [42 nm:401 nm] | inside window | 309.04 | Very slight to no cracking at center of swatch (the most flexed portion)—microscope needed for observation. [c] |

[c] In some cases the film separated from the leather, and appeared to have cracked but was not.

The data demonstrate the following: As the proportion of hard polymer increases in the binary blend, the tack (acquired as described previously) decreases, the storage modulus, G', increases and Bally Flex Test results trend to more cracking.

The Bally Flex Test (Otherwise Known as Flexing Endurance of Coated Leather) is Defined as Follows:

The flexing endurance under wet or dry conditions is based on the IUF 20 method of International Union of Leather Chemists Association using a Bally Flexometer (Bally SchuhFabriken AG, Schoenenwerd, Switzerland). The dry (or wet) leather specimens (65 mm. by 40 mm.) were flexed and examined for damage typically after 20,000, and 100,000 flexes. Each sample was run in duplicate. We noted the condition of the coated leather swataches after 100,000 flex cycles and recorded the appearance by using an unaided eye or a microscope under 10-100× magnification focused on the most flexed area of the swatch. The extent of damage sustained is dependent on the toughness and flexibility of the polymer, but adhesion to the leather itself can play a role and introduce an additional variable. The type of leather can be a factor also. Full grain leather with the smoothest finish possible was typically employed in these studies. Coatings of the polymer were typically applied by hand and spread with an applicator stick to a constant coating weight, although we acknowledge that soakage into the leather will cause discrepancies in film thickness from sample to sample. It was our assessment that very slight to no cracking in this test was a good indication that the polymer would endure well on skin, especially those parts of the body where flexibility is important such as the hand area between the thumb and forefinger. We achieved positive correlation with subjective wear tests and good Bally Flex results.

Graph of Inventive Polymer Film examples vs. Comparative Films, showing that Comparative Films also fall in the Theologically defined window.

| Sample ID | Comment |
|---|---|
| Pure Soft, 94 nm | Single polymer system that fits in the rheological window |
| 20:80 Hard:Soft [94 nm:94 nm] | Fits in rheological window and is to be compared to the 20:80 Hard/Soft blend that utilizes 40 nm hard and 401 nm soft particles, with lower tack (previous Tack example). |
| Competitive Product #1 | This uses cyanoacrylate chemistry and is on the lower end of the G' scale, rendering it suseptable to dirt pickup (tacky). Wear tests indicate this. |
| Competitive Product #2 | This is a silicone-based polymer system, rendering it low tack but it utilizes chemistry different from the current invention. It also falls in the window. |
| Competitive Product #3 | This is a solvent acrylic based polymer system utilizing stinging solvents and is also on the low range of the G' storage modulus window, rendering it susceptible to dirt pick-up, as in-house wear tests indicate. |
| 20:80 Hard:Soft [42 nm:401 nm] | This is a low tack blend that forms a tough durable film, on the high side of the ap[plicable window. Note that by tailoring the blend ratio with the differential sizes, one can custom design a system to suit the formulation ingredients and end-use. |

DSM measurements demonstrates that films prepared from the hard:soft blends have different dynamic storage modulus values at 37° C. between $T_g$ values for the respective hard and soft components. The values of G' at 37° C. decrease systematically with increasing amounts of the soft component. The existence of two $T_g$ values is better demonstrated in tan δ curves as a function of temperature, which exhibit two peaks corresponding to the two $T_g$ values. The peak positions in tan δ are related to the $T_g$ values of each component of the blend and the relative intensities of the two peaks is related to the composition of the blend. Analogous plots for blends prepared using a "softer hard" (lower Tg) hard component were measured. For equivalent compositions, the lower $T_g$ hard material produces lower dynamic storage modulus values at 37° C. than the higher $T_g$ hard material. This set of measurements demonstrates the desired rheological properties can be achieved by varying the composition of the hard:soft blend and by varying the $T_g$ values of the blend components at different ratios. The optimum ratio of the hard and soft components varies with the $T_g$ values of the individual components.

What is claimed is:

1. An aqueous film forming composition that adheres to mammalian skin and related substrates comprising: a aqueous dispersion of blend of two or more polymers comprising a) from 10 to 30% by weight of one or more hard polymers having a Tg of 40 to 75° C. and an average particle size greater than 30 nm; and b) from 70 to 90% by weight of one or more soft polymers having a Tg of 0 to 37° C. and an average particle size of 360 to 800 nm; wherein the polymer blend at 37° C. has a range of dynamic storage modulus of from $5 \times 10^4$ and $1 \times 10^8$ dynes/cm$^2$ at a frequency of $10^{-1}$ rad/sec to a corresponding dynamic storage modulus of from $1 \times 10^6$ and $1 \times 10^8$ dynes/cm$^2$ at a frequency of $10^2$ rad/sec.

2. The aqueous film forming composition according to claim 1, further comprising one or more active agents selected from the group consisting of pharmaceutical agents, antimicrobial agents, cosmetic agents, skin care agents and combinations thereof.

3. The aqueous film forming composition according to claim 1, further comprising one or more inorganic solids selected from silica and colloidal silica.

4. The composition of claim 1 wherein the average particle size of the hard polymers is smaller than the average particle size of the soft polymers.

5. The aqueous film forming composition according to claim 1, further comprising one or more ethylenically unsaturated surfactant monomers.

6. A medical adhesive comprising the composition of claim 1.

7. A film that adheres to mammalian skin and related substrates comprising an aqueous dispersion of a blend of two or more emulsion polymers mammalian skin and related substrates, the polymer blend comprising: a) from 10 to 30 % by weight of one or more hard polymers having a Tg of 40 to 75° C., and an average particle size greater than 30 nm and b) from 70 to 90% by weight of one or more soft polymers having a Tg of 0 to 37° C., and an average particle size of 360 to 800 nm; wherein the polymer blend at 37° –C. has a range of dynamic storage modulus of from $5 \times 10^4$ and $1 \times 10^8$ dynes/cm$^2$ at a frequency of $10^{-1}$ rad/sec to a corresponding dynamic storage modulus of from $1 \times 10^6$ and $1 \times 10^8$ dynes/cm$^2$ at a frequency of $10^2$ rad/sec.

8. The film of claim 7 wherein the average particle size of the hard polymers is smaller than the average particle size of the soft polymers.

9. A film forming medical article that adheres to mammalian skin and related substrates comprising: an aqueous dispersion of a blend of two or more emulsion polymers, the polymer blend comprising: a) from 10 to 30-% by weight of one or more hard polymers having a Tg greater than 370° C., and an average particle size greater than 30 nm and b) from 70 to 90% by weight of one or more soft polymers having a Tg of 0 to 37° C., and an average particle size of 360 to 800 nm; wherein the polymer blend at 37° C. has a range of dynamic storage modulus of from $5 \times 10^4$ and $1 \times 10^8$ dynes/cm$^2$ at a frequency of $10^1$ rad/sec to a corresponding dynamic storage modulus of from $1 \times 10^6$ and $1 \times 10^8$ dynes/cm$^2$ at a frequency of $10^2$ rad/sec; and wherein the film forming medical article is permeable to air and water, durable and washable.

10. A liquid emulsion bandage formed from the film forming medical article of claim 9.

11. The film forming medical article of claim 7 further comprising one or more active agents.

12. The film forming medical article of claim 11, wherein the active agents are selected from the group consisting of antimicrobial agents, pharmaceutical agents, cosmetic agents, skin care agents, and combinations thereof.

13. The article of claim 9 wherein the average particle size of the hard polymers is smaller than the average particle size of the soft polymers.

* * * * *